United States Patent
Payton

(10) Patent No.: US 6,827,574 B2
(45) Date of Patent: Dec. 7, 2004

(54) SKELETAL TRANSMUCOSAL ORTHODONTIC PLATE AND METHOD

(76) Inventor: Kevin L. Payton, 507 Oleander Dr., Hallandale, FL (US) 33009

(*) Notice: Subject to any disclaimer, the term of this patent is extended or adjusted under 35 U.S.C. 154(b) by 0 days.

(21) Appl. No.: 09/833,898

(22) Filed: Apr. 12, 2001

(65) Prior Publication Data
US 2002/0150856 A1 Oct. 17, 2002

(51) Int. Cl.[7] .................................................. A61C 3/00
(52) U.S. Cl. ............................... 433/8; 433/18; 433/173
(58) Field of Search ............................ 433/8, 9, 17, 18, 433/173, 24

(56) References Cited

U.S. PATENT DOCUMENTS

| 4,923,471 A | 5/1990 | Morgan | 623/16 |
|---|---|---|---|
| 5,052,930 A | 10/1991 | Lodde | 433/173 |
| 5,066,224 A | 11/1991 | Block | 433/7 |
| 5,538,427 A | 7/1996 | Hoffman | 433/173 |
| 5,853,291 A * | 12/1998 | DeVincenzo et al. | 433/176 |
| 5,921,774 A * | 7/1999 | Kanomi et al. | 433/18 |
| 5,938,437 A * | 8/1999 | DeVincenzo | 433/18 |
| 6,001,099 A | 12/1999 | Huebner | 606/99 |
| 6,193,509 B1 * | 2/2001 | DeVincenzo | 433/18 |
| 6,354,834 B2 * | 3/2002 | Konomi et al. | 433/18 |

* cited by examiner

Primary Examiner—John J Wilson
(74) Attorney, Agent, or Firm—Malin, Haley & DiMaggio, P.A.

(57) ABSTRACT

An orthodontic appliance anchored to the bone of the patient's mouth, the appliance having a wire guide for use with orthodontic tension bands to alleviate the use of other teeth as anchors. The device and method utilize a thin plate anchor body having at least one aperture, a bone fastener receivable through the anchor body aperture, and a tension band and/or wire guide channel affixed to the anchor plate body.

5 Claims, 5 Drawing Sheets

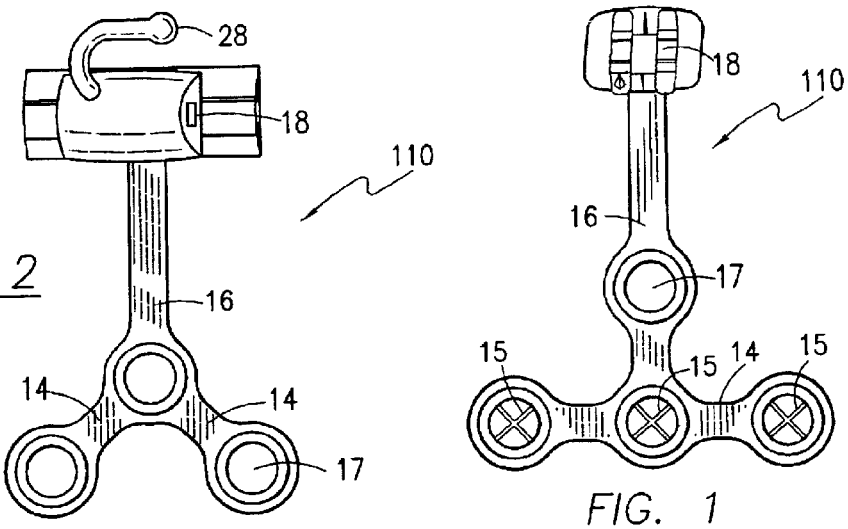
FIG. 2
FIG. 1
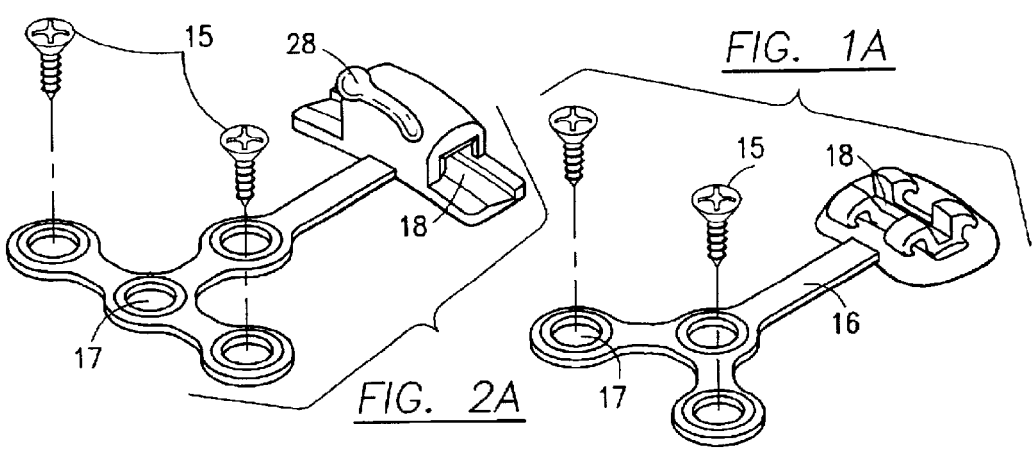
FIG. 2A
FIG. 1A
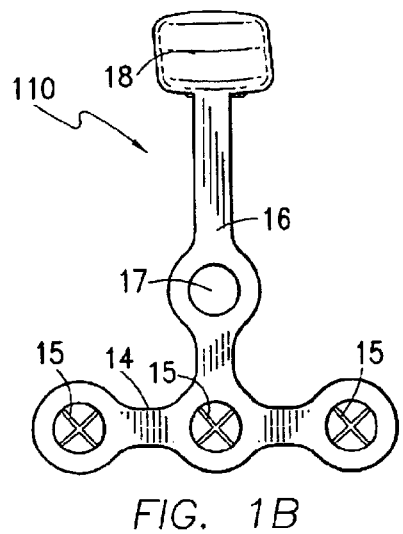
FIG. 1B

SKELETAL TRANSMUCOSAL ORTHODONTIC PLATE AND METHOD

BACKGROUND OF THE INVENTION

1. Field of the Invention

This invention relates generally to an orthodontic appliance, and more particularly to an orthodontic bone anchor that can provide tension usable as fixed pushing, pulling or stabilizing points by the orthodontist in treating the malalignment of the teeth of a patient without disturbing adjacent teeth.

2. Description of Related Art

In traditional tooth movement, orthodontic brackets are placed on the teeth, and the brackets are connected to one another using orthodontic archwires. The orthodontic archwire in conjunction with tension bands guides and provides tooth-moving forces to certain teeth, using other teeth as anchors. This traditional method of tooth movement however, has several potential shortcomings. For example, in some patients, the tooth or teeth to be used as an anchor may be missing. Furthermore, although a particular tooth may be serving as an anchor in resisting an orthodontic force, in reality the tension band on the teeth being moved also will exert a counter-force on this "anchor" tooth which may cause undesirable movement of the anchor tooth.

Therefore, in treating many orthodontic patients, it is desirable to move some teeth yet stabilize other teeth which otherwise would move due to the reactive forces created in the mouth. Traditionally, this tooth stabilization, or differential tooth movement, has been achieved by applying lower forces in the mouth or by utilizing several teeth as the anchor. However, when lower forces are applied, orthodontic treatment requires significantly more time, and when several teeth are used in combination as an anchor, the resulting tooth-moving response may be somewhat unpredictable.

All orthodontic forces adhere to Newton's "Law of Reciprocal Forces." If a tension band force is applied to retract or pull back an object such as a tooth, there exists an "equal and opposite" force to move another tooth or object forward. The resistive force value of the teeth is known as anchorage. Orthodontists may offset these reciprocal tendencies by using an extraoral force known as a headgear to augment the resistive force value of the teeth and as a way of obtaining differential tooth movement. Patient compliance is often inadequate as many patients do not want to wear the headgear. Poor compliance compromises orthodontic therapy and often the final result. Orthodontic forces are usually continuous, acting 24 hours a day. Realistically, most patients will not wear headgear more than 10–12 hours/day. Therefore, the posterior anchorage is typically fortified only 40–50% of the time. All too often, inconsistent usage or overt noncompliance will reduce this effect even more.

Endosseous implants which are placed deeply into bone, are useful when physical space within the mouth is available such as through absence of a molar, however, their use is limited in full dentition where space is at a premium. Endosseous implants are also not suitable in juvenile or adolescents because they are inserted into a hole which is drilled into the alveolar (tooth bearing) portion of the jawbone. Insertion of an endosseous implant into these areas will harm unerupted teeth forming in these areas. Since the juvenile and adolescent patients are still growing, an endosseous implant will be engulfed with continuing vertical development of the alveolar bone and will progressively sink to a lower level thereby becoming inaccessible and difficult to remove.

Subperiostal bone anchors have been known and used in dentistry for many years and their value in orthodontics has been acknowledged since at least the mid 1980's (Turley, J. Dent. Res. 63A:334, 1984). These bone anchors can be attached to bone just about anywhere in the mouth with little, if any likelihood of destruction of bone or teeth. Block and Hoffman first patented (Block, Orthodontic Anchor U.S. Pat. No. 5,066,224; Hoffman, Subperiosteal Bone Anchor; U.S. Pat. No. 5,538,427) then later published (Am. J. Orthod. Dentofac. Orthop. 107:251,1995) an orthodontic anchorage system that did not penetrate the bone as endosteal implants do but merely rested on the surface of the bone.

One of the difficulties with some of the prior art is that the devices were rigid, thick and are not moldable to the unique bone morphology found at the surgical site or into a desired direction. Further, the bone-anchor interface surface was often times very complex, being shaped to allow and foster bone ingrowth. After the many weeks for the prior art to osseointegrate, a further surgical procedure is necessary to uncover a portion of the anchor and attach an extruding abutment.

It will therefore be understood that the prior devices are rigid, cannot be adapted to irregular bony contours at the time of surgery, are somewhat bulky and thus limit intraoral placement to locations where overlying soft tissue is relatively thick, such as in the palate, and require two separate surgical procedures. Additionally the attachment procedure connecting the device to teeth is complex and often requires additional laboratory steps.

In the last 10 years small bone plates in numerous configurations have come into high use in orthognathic and maxillofacial reconstructive surgery with such plates being deformable and contourable to fit to a variety of irregular bony surgical sites. Contourable bone plates of "Y", "T", "L" and "I" shape configurations, and of more complex geometrical shapes, are available in a variety of thicknesses and with a selection of degrees of malleability.

U.S. Pat. No. 5,853,291 to Vincenzo discloses a thin, subperiosteal bone anchor for use in conjunction with orthodontic appliances having a plurality of moldable, scalloped leaves and arms to facilitate bone overgrowth and an upwardly extending stem with a variety of attachment connection mechanisms. The entire base and leaves of the anchor are scalloped to foster osteointegration. A sphere or rectangular tube projects upward. This anchor, although small, thin and moldable to bone, is highly three dimensional with its orthodontic attachment rising up from its planar fixation against the bone, is structured with tapering, leaf-like projections to foster osteointegration, whereas the present invention is in substantially a planar configuration when in use, is designed to be temporary and without osteointegration, includes a tension band holder and wire guide integrally fixated thereon which are structured to receive and attach other orthodontic adjustment and attachment devices and requires less traumatic surgical procedures to remove, thus has less morbidity to the patient.

The plates readily usable in orthognathic and maxillofacial surgery, as described above, are generally relatively small (about 20–40 mm. in their major dimension). These small, malleable bone plates, often made of a titanium alloy contain a plurality of holes situated over the surface through which standard bone screws and fasteners can pass to attach the plate to bone and through which archwire can be threaded when attaching the distal end of the plate stemarm to orthodontic appliances within the mouth of the patient. Although the small, moldable bone plates function as adequate anchors and do not osteointegrate, the stemarm portion with only holes for attachment to other orthodontic hardware in the patient's mouth provide limited directional torque and control thereby restricting treatment options, compromising outcome, and often prolonging treatment time. These miniature prior art bone plates can be obtained from a variety of suppliers, e.g. KLS Martin, L. P. of Jacksonville, Fla., see pages 7–9, 35–37, 48, 58–60, 74–77, 101, and 102 of their Surgical Instrument Catalog, 1st edition, for examples and from W. Lorenz of Jacksonville, Fla., see pages 4, 5, 7, 10, 12, 17, 19, 20, 29, and 30 of the 1988 Surgical Instrument Catalog for examples.

In the orthodontic field a need exists for a non-osteointegrating, bendable temporary bone anchor and tension band connector for resisting tension band forces of the tension band attached to a tooth to be moved that includes enhanced directional tension band torque and control, which is installed and removed with minimal surgical trauma, morbidity and healing time. Other teeth not to be moved are not used as anchors.

BRIEF SUMMARY OF THE INVENTION

More particularly, the system includes a flat, rigid body referred to hereinafter as an anchor plate, having a base and one or more arms and at least one aperture through which a screw is positioned to affix the bone plate to the cortical surface of bone attachable at various oral locations, e.g. buccal, labial, lingual and palatal surfaces of the maxillary jawbone and the buccal, labial and lingual surfaces of the mandibular jawbone. An orthodontic tension band bracket, having up to four prongs, is integrally fixated to the rigid body opposite the body arm. The tension band bracket protrudes substantially vertically from the gum substantially parallel to the tooth line but not on an occlusal surface. The arm of the rigid body is surgically fastened to the bone, preferably with bones screws and in 5–7 days when the soft tissue incision has healed, the tension band bracket on the distal end of the rigid body is then attached by a tension band to at least one other orthodontic tension bracket within the patient's mouth. A guide wire passage can also be affixed to the anchor body. The tension band bracket on the rigid anchor body not only provides multi-directional tension attachment options, but also multi-directional torque based on physical placement in the mouth and selection of the type of tension or guide integrally connected thereto. The guide tube may be connected by rectangular or cylindrical wire. Using the tension band prongs, the anchor body can accommodate elastic bands or thread, chains, springs or by any other suitable type of releasable tension force mechanism or device commonly used in orthodontics. The anchor plate body can also be utilized as anchorage in the space of a missing tooth. It is preferred that the anchor body arm and tension band bracket wire and guide tube be unitarily formed as a single component, but could be separately fixated together as well using different manufacturing compositions so long as the final device is biocompatible and durable.

The rigid anchor body should be thin to lay under the soft tissue against the bone without being bulky and should not osteointegrate. The system serves as an anchor in the mouth usable without prolonged healing and recuperative time after surgical installation and removal and without significant morbidity to the patient. The anchor body is manually moldable to conform to individual bone curvature and into areas difficult to reach. The system is particularly useful where there has been a loss of posterior teeth and thus posterior anchorage and can be used in substantially all patient populations. Because of the increased torque and control and the ability to move teeth in virtually all directions, overall treatment time is reduced.

It is an object of this invention to provide a tension band anchor and wire guide for moving one or more teeth under tension, avoiding the use of other teeth as anchors when movement of such other teeth during treatment is undesirable.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 1 is a front elevational view of one embodiment of the present invention.

FIG. 1A is a perspective view of the embodiment shown in FIG. 1.

FIG. 1B is a rear elevational view of the embodiment shown in FIG. 1.

FIG. 2 is a front elevational view of the preferred embodiment of the present invention.

FIG. 2A is a perspective view of the preferred embodiment shown in FIG. 2.

FIG. 11A through E are perspective views of five prior art orthodontic tubes.

PREFERRED EMBODIMENT OF THE INVENTION

Figure 6:
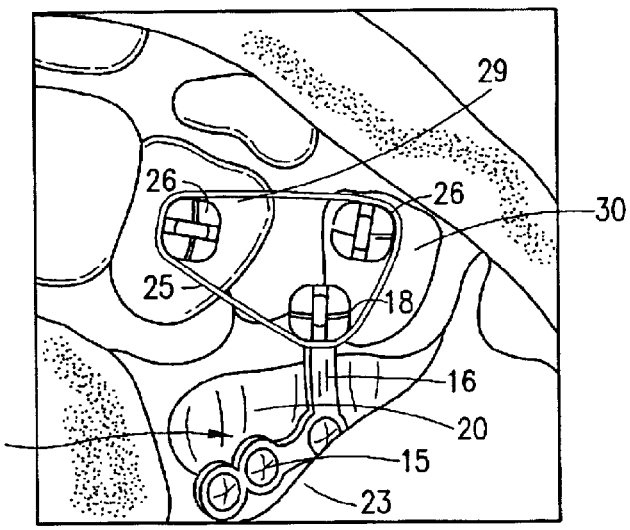
FIG. 6 is a perspective view of the present invention installed in the mandible and bent into selected conforming position in use where teeth are missing.

Referring now to the drawings, and in particular to FIG. 1, guide anchor plate 110 is shown having a bendable, malleable, substantially thin, planar base 14 shown in the form of a T-shaped body. Anchor plate 110 comprises an elongated straight body central member 16 which, after installation, protrudes through the soft tissues of the gum substantially adjacent a lateral side of the dentition as shown in FIG. 6. The anchor body base 14 unitarily formed at one end of central member 16 includes one or more apertures/openings 17 (preferably at least two) extending through the base 14 and adapted to receive one or more fasteners 15, preferably screws, the heads of which will be flush with the top surface of the base 14. The base 14 and central member 16 are bendable to conform to bone contour to directionally fit a desired space. The fasteners 15 situated within the openings 17 anchor the base 14 against the bone, either mandible or maxilla, such that the base 14 lies firmly flush, preferably in conforming engagement against the bone, in the selected location just under the periosteum and other soft tissues. The central member 16 extends from the base 14 through the soft tissues 23 substantially beside the tooth but not so as to interfere with the occusal surface of the teeth and positioned at a level and angle in the judgment of the orthodontist and oral surgeon which is sufficient to provide the desired directional movement and anchorage. A wire guide 18 is integrally affixed to the distal end of central member 16. The wire guide 18 receives a square or round orthodontic wire for use with other wire guides affixed to certain teeth. The wire guide 18 may be merely affixed to the distal end of the central member 16 without being integrally configured, but such an arrangement is not preferred.

It is important to note that the anchor body including base 14 and central member 16 are small and thin and the invention contemplates a variety of shapes, such a "T", "L", "S", "Y", "U", "H", "X", "W", "Z", double "Y", longitudinal, and double "T", or other shapes suitable for service as a guide wire anchor and a tension band bracket anchor. The shape of the orthodontic anchor plate depends upon the kind of tooth movement sought, e.g. distalization, extrusion, or intrusion, the number of teeth to be moved, the space available, and the location within the mouth at which the plate 110 is to be attached. FIG. 1A shows the central member 16, the base 14, including openings 17 and fasteners 15, along with wire guide 18.

A variety of orthodontic and miniature/mini-bone plates are known, four examples of which are shown in FIGS. 8A, 8B, 8C, and 8D. These prior art bone plates are currently manufactured and readily obtainable from companies such as KLS Martin L. P. of Jacksonville, Fla. and Walter Lorenz Surgical Instruments, Inc. of Jacksonville, Fla., just to name a few. Titanium or a titanium alloy is the preferred metal, however any moldable, durable biocompatible material could be used so long as the material could withstand sufficient shear forces to serve as an anchor.

Figure 3:
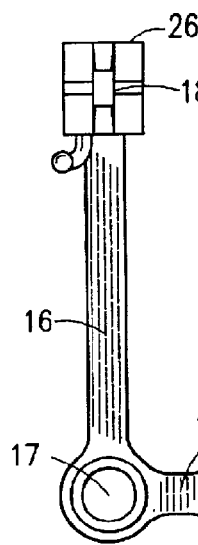
FIG. 3 is a front elevational view of a third embodiment of the present invention.
Figure 4:
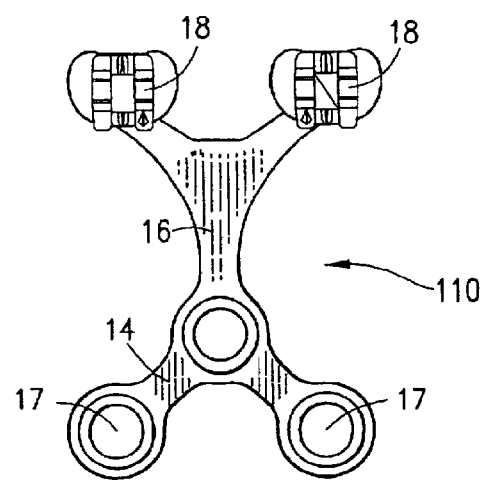
FIG. 4 is a front elevational view of a fourth embodiment of the present invention.
Figure 5:
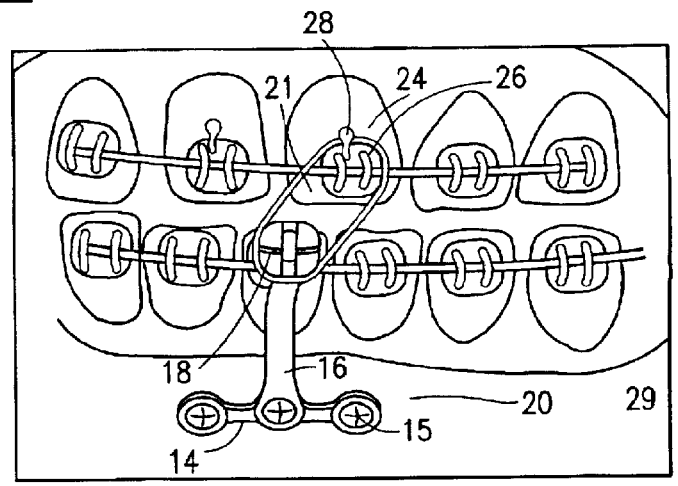
FIG. 5 is a side elevation view of one embodiment of the present invention attached to the mandible and in use with a tension band prong.

In view of the construction of the plate as shown in FIGS. 5 and 6, it will be understood by those skilled in the art that the plate 110 of the present invention will be secured against the bone 20, shown in these figures as mandibular bone, in the selected location. As the plate 110 is placed, the base 14 can be bent to conform to the shape of the surface of the bone 20 and the central member 16 bent in the direction and at the angle desired for optimal attachment to and for movement of the tooth. Further, one or more fasteners 15 will be passed through the opening(s) 17 in base 14 to securely pull the base down firmly against the bone. The periosteum and other soft tissues will then be surgically closed in the customary manner over the base of the device leaving at least one central member 16 protruding through the soft tissue 23. As a result, when the tissue heals, the wire guide 18 at the distal end of the central member 16 is ready to be connected using orthodontic wire, chains, or threads to other orthodontic appliance bracket(s) 26 or tube(s) on the patient's teeth (for example) without the need for a second surgical procedure. The orthodontia can then be adjusted as needed and in the customary manner by the orthodontist.

In FIG. 5, a T-shaped plate with single bracket 18 at the distal end is fixed to the cortical portion of the bone 20 by screws 15. Then the wire guide 18 is attached by an elastic band 21 looped around the prong 28 of bracket 26 of maxillary canine 24 to accomplish the goal of supereruption of the maxillary tooth.

In FIG. 6, a buccally fixated bone plate 110 is secured to mandibular bone 20 beneath the space created by a missing mandibular bicuspid using screws 15. The central member 16 is bent out toward the cheek for proper fit. Tooth 29 is moved by looping elastic 25 around the wire guide 18 and the brackets 26 on the teeth 29 and 30, with the goal being to close the space between the teeth and achieve correct alignment. The bendability of the plate and central members allow adaptability to the various bony configurations and directional needs in the mouth.

Figure 7:
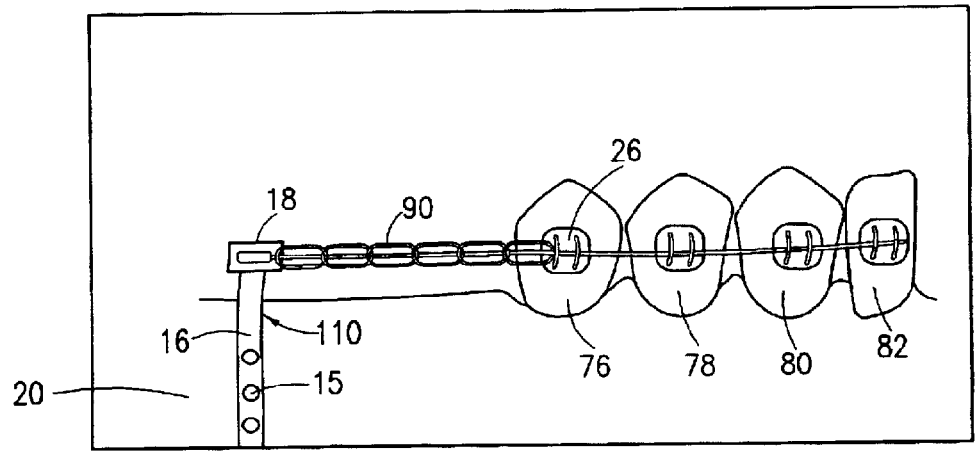
FIG. 7 shows a side elevation view of the present invention using a chain connected to anterior mandibular dentition over space created by several missing posterior teeth.
Figure 8:
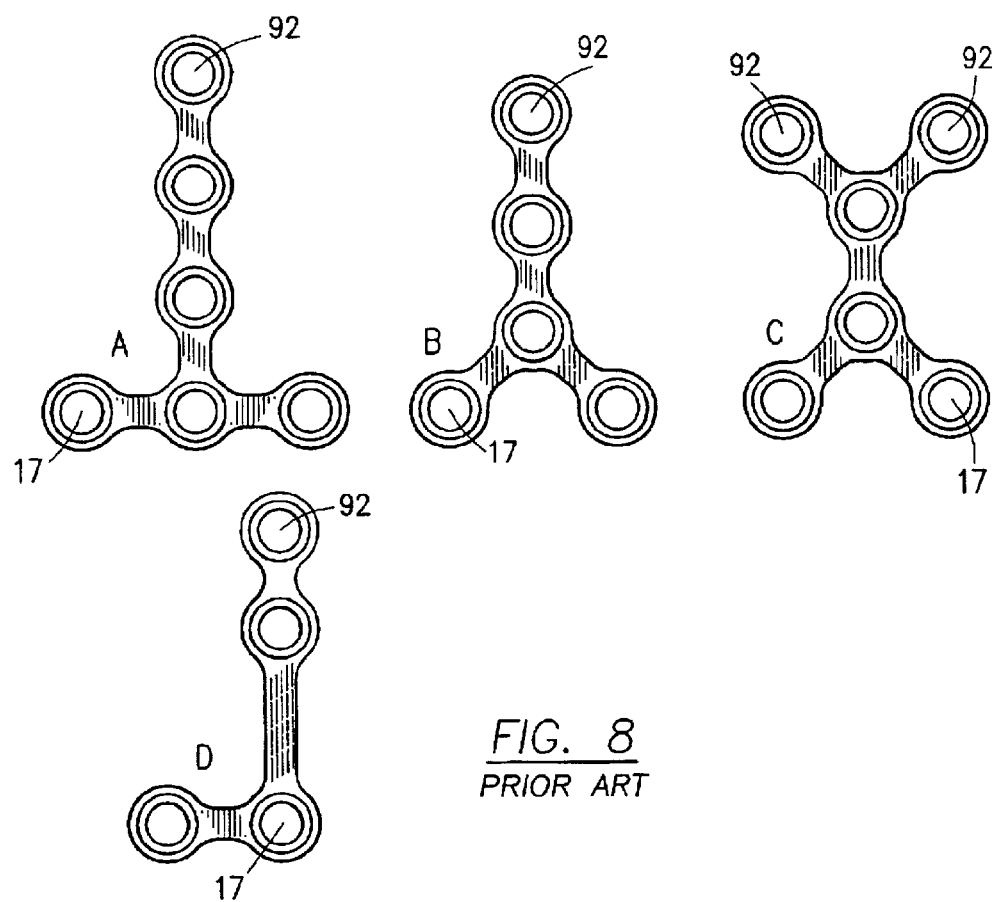
FIG. 8A through D is a front elevational view of four representatives of prior art miniature bone plates.

The present invention can also be used in partially edentulous patients when few, if any anchoring teeth exist as shown in FIG. 7. Distalization of anterior mandibular teeth 76, 78, 80, and 82 is accomplished using a longitudinal bone plate 110 attached in a vertical position in the posterior portion of the bone 20 for anchorage, the wire guide 18 at the distal end of the central member 16 of the plate 110 is attached by chains 90 to bracket 26 on the nearest anterior tooth 76, which is attached with wire to brackets on other abutting anterior teeth 78, 80, and 82.

Figure 9:
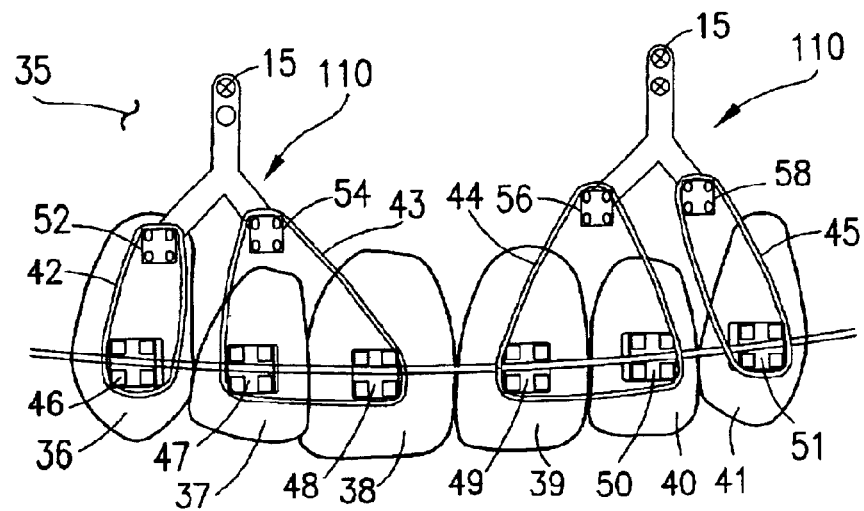
FIG. 9 shows a side elevation view of the present invention in use on maxillary dentition.

In FIG. 9 an anchor plate 110, with base 14 is secured with screws 15 against the bone 20, shown here as maxillary bone, leaving the central member 16 with wire guide 18 protruding through the soft tissues. Archwires 64 and 66 attach to wire guide 18 and also connect to brackets 68 and 70, respectively, affixed to maxillary molars 72 and 74, respectively, to produce torque in the superior direction for intrusion of the maxillary molars 72 and 74 to close an open bite deformity.

Figure 12:
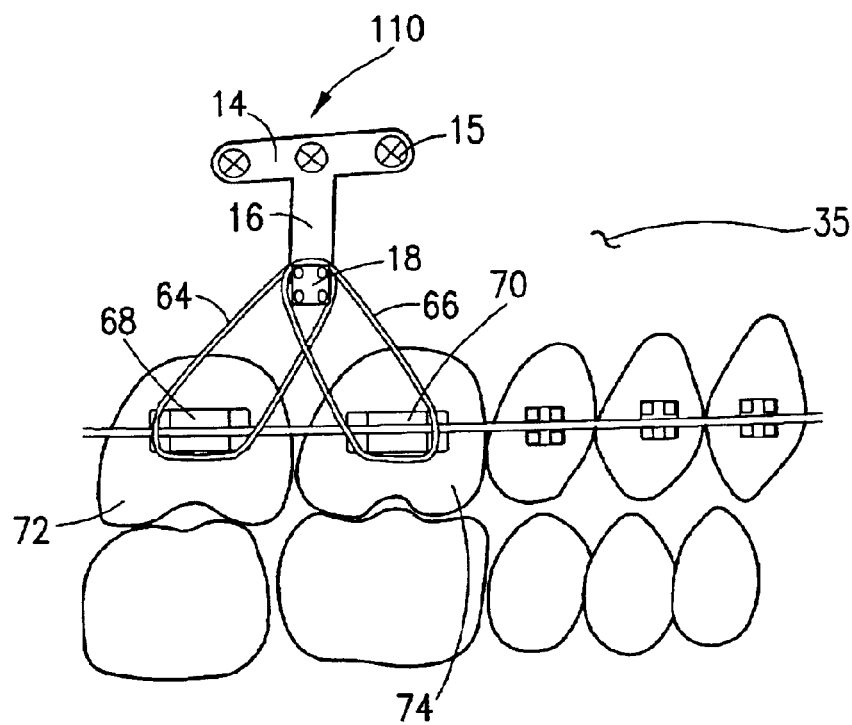
FIG. 12 shows a front elevation view of the present invention in use on anterior maxillary teeth.
Figure 10A:
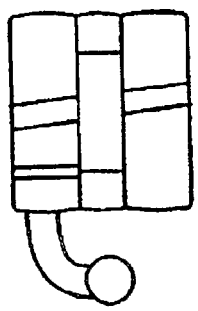
FIG. 10A through D are front elevational views of four prior art orthodontic brackets.
Figure 10B:
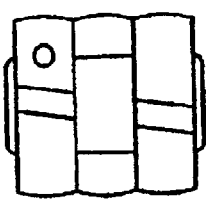
Figure 10C:
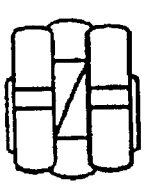
Figure 10D:
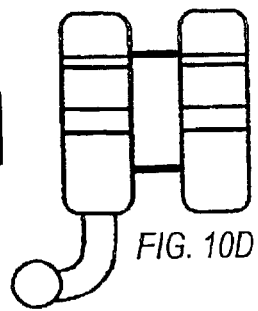
Figure 11A:
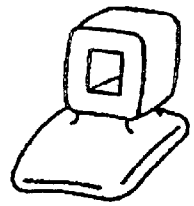
Figure 11C:
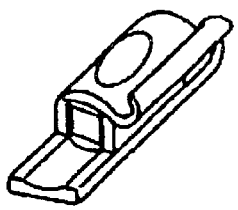
Figure 10E:
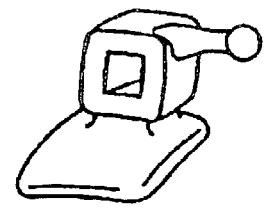
Figure 11B:
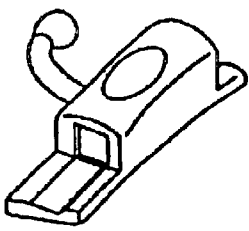
Figure 11D:
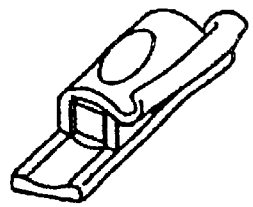

There are times when one or more teeth have extruded because of a lack of tooth or teeth contact from the opposing arch. When this occurs it is nearly impossible to intrude the tooth or teeth back to their desired positions(s). An example of the plate accomplishing such movement is shown in FIG. 12 where two anchor plates 110 are secured high up onto maxillary bone 35 using fasteners 15 to create upwardly directed torque to intrude maxillary incisors 36–41. Archwires 42–45 connect brackets 46–51, respectively, to stemarm wire guides 52, 54, 56, and 58, respectively. The reverse configuration (not shown) to extrude maxillary teeth, for example, would require plate placement low on mandibular bone with pronged brackets utilizing elastics connected from the plate brackets up to the brackets on the maxillary teeth to be extruded. The same type of connection to extrude mandibular teeth could be used with the plate attached high on the maxillary bone.

Instead of wire being threaded through a distal hole 92 of the stemarm of prior art anchors shown in FIGS. 8A, 8B, 8C, and 8D, the present invention's orthodontic wire guide, such as a bracket or tube, integrally molded or separately affixed at the distal end of the central member 16, improves anterior and posterior movement of teeth, provides a point of anchorage when teeth are missing, and increases directional torque and control, all while utilizing devices and techniques with which an orthodontist is familiar.

Thus, the present invention provides a subperiosteal orthodontic system temporarily fixated against the cortical surface of the bone situated underneath the soft tissues of the oral cavity. The base and central member(s) may be bent at the time of surgery to conform to the receiving bone and the direction of alignment sought. The base is then preferably screwed, nailed, or securely fastened down to pull the plate into firm, conforming engagement against the bone. The central member, having a bracket or tube fixated at the distal end, protrudes through the soft tissues. After the tissue heals, the wire guide can be attached via wire, chains, springs, elastic bands or thread, or other known, customary orthodontic method or technique of attachment to the desired orthodontic appliance within the mouth of the patient. One or more anchor plates may be used to provide proper anchoring, directional torque and control as needed in the collective judgment of the orthodontist and oral surgeon.

The maximum dimensions of the anchor plate 110 are only limited by the size and location of the area on which the plate is to attach and the thickness being that which will not create excessive bulk under the soft tissue. The orthodontic appliance, e.g., wire guide or tube, at the distal end of the central member is of the type and size customarily utilized in the field of orthodontics.

The structure of both the anchor plate 110, wire guide 18, and tube 19 is preferably titanium or titanium alloy, however, stainless steel or other biocompatible materials can be used. The wire guide 18 and tube 19 are preferably integrally molded at the distal end of the central member 16 of the anchor plate 110, however, other methods of attachment and permanent fixation of these two surfaces generally accepted in the industry and usable orally may be employed. The surface of the orthodontic plate is smooth. The central member 16 may be solid or may have openings 112 therethrough except at the distal end where the orthodontic appliance, e.g. wire guide 18, tube 19, is affixed.

Orthodontic brackets and tubes currently available as shown in FIGS. 10A through 10D and 11A through 11E, respectively, are generally constructed of stainless steel. Although according to this invention, a standard stainless steel bracket could also be fixedly attached to a standard titanium or other biocompatible bone plate, via soldering, glue, or other permanent fixation method known within the art, after each is separately manufactured, it is believed that the sheer strength of the completed apparatus would be less and cost of manufacture and potential for incompatibility may be higher than with unitary molding. This unitary molding may also allay possible concerns within the medical/dental community of biocompatibility, durability, structural integrity, and compliance with guidelines of the Food and Drug Administration in the United States.

The anchor plate 110 is able to resist both primary lateral and horizontal forces as well as a vertical force and may be used with any conventional orthodontic appliance.

The anchor plate 110 is installed into a patient's mouth in accordance with the following procedures. These are generalized for an understanding of the invention, and are not the detailed procedures which would be actually followed by a surgeon.

Under local anesthesia, an incision will be made and a subperiosteal tunnel created so that the tunnel will place the plate at the desired location. One or more anchor plates may be placed depending on the treatment needs of the patient. The plate(s) will be placed into the subperiosteal tunnel directly against the bone and secured preferably by screws. One or more central members having orthodontic wire guides or tubes at the distal end will be left protruding through the gum. The soft tissue incision will be closed using standard oral surgical techniques. The placement of the plates generally takes only about 10 minutes per plate. Saline rinses, mild antiseptic mouthwashes and thorough brushing of teeth usually control any mild infections, however, some patients may require antibiotics and analgesics, based on the judgment of the surgeon. This surgical procedure causes minimal pain and swelling to the patient. Approximately 5–7 days later, after the incision has completely healed, the wire guide or tube at the distal end of the plate's central member is wired or otherwise attached to orthodontic appliances on the teeth, placed in such a way that the wire attaching the guide wire or tube to the tooth acts as an anchor to hold the desired tooth in place or to move teeth or as a substitute anchoring point where teeth are missing. The plate will serve as the point of absolute anchorage, preventing movement of the anchored teeth. The remaining dentition will be treated with conventional orthodontic appliances where indicated.

At the conclusion of the orthodontic treatment utilizing the skeletal transmucosal orthodontic plate, the plate is removed. Under local anesthesia, an incision is then made exposing the entire orthodontic bone plate. The screws or other fixation elements are removed along with the plate. The incision is closed using conventional oral surgical techniques and procedures. Saline rinses may be used to aid healing.

Those skilled in the art should understand that the directions used herein, such as top, bottom, up, and down are relative to the bone on which the plate is being mounted. The bone is always at the bottom, and "up" is away from the bone and "down" is towards the bone. The anchors or plates, of the present invention may be mounted in any direction with respect to the earth. The term "vertically" should be understood as toward the top of the head or substantially perpendicular to the earth. The term "horizontally" should be understood as substantially parallel to the earth. "Out is intended to mean toward the cheek and "in" means toward the tongue or palate area. The above mentioned directions are used for clarity of description.

It will thus be seen that the objects set forth above, among those made apparent from the preceding description, are efficiently attained and, since certain changes may be made in carrying out the above method and in the article set forth without departing from the spirit and scope of the invention. It is intended that all matter contained in the above description and in the accompanying drawings shall be interpreted as illustrative and in not a limiting sense as numerous variations are possible and no single feature, function or property of the preferred embodiment is essential.

It is also to be understood that the following claims are intended to cover all of the generic and specific features of the invention herein described, and all statements of the scope of the invention which, as a matter of language, might be said to fall therebetween.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A method of orthodontic anchorage for use as a fixed pushing, pulling or stabilizing point in treating teeth and bite malalignments, said orthodontic system to avoid subperiodontal healing time and ossocointegration for immediate use, the method comprising:

(a) providing a flat, rigid body, comprising:
 a bendable base having at least one aperture adapted to receive at least one fastener for affixing said base to the bone;
 at least one bendable elongated central member planarly extending from said base, the distal end of said central member having a first orthodontic appliance integrally formed thereto and adapted to receive wire for attachment to a second orthodontic appliance attached to a patient's tooth;

(b) making an incision in the oral soft tissue at the desired placement location to expose the bone on which said base is to be attached;

(c) securely anchoring and affixing said base to the bone with at least one bone fastener not utilizing subperiodontal ossocointegration so that the base contacts the bone and the central member extends through the soft tissue of the jaw adjacent a non-occusal surface of the teeth;

(d) affixing said first orthodontic appliance to at least a second orthodontic appliance attached to at least one tooth in the patient's mouth using orthodontic wire;

(e) adjusting said wire periodically until teeth or bite malalignment is corrected as determined by the orthodontist;

(f) after completion of the orthodontic treatment, disconnecting said first orthodontic appliance from said second orthodontic appliances, making an incision at the insertion site to reveal the base, unfastening and removing said base, surgically closing the incision and allowing the incision site to heal.

2. The method of claim 1, wherein said first orthodontic appliance is an orthodontic wire guide.

3. The method of claim 1, wherein said first orthodontic appliance is an orthodontic tension band bracket.

4. The method of claim 1, further including chains, elastics, springs, or thread connected between said first orthodontic appliance and a second orthodontic appliance positioned within the patient's mouth.

5. A method of orthodontic anchorage for use as a fixed, pushing, pulling or stabilizing point in treating teeth and bite mal-alignments, said orthodontic system to avoid subperiodontal healing time and ossocointegration for immediate use, the method comprising the steps of:

(a) providing a substantially flat, thin, rigid bone anchor plate for anchoring an orthodontic appliance rigidly attached to said bone anchor plate to a patient's bone; said bone anchor plate having a bendable base and at least one aperture for receiving a bone anchor fastener for affixing said plate to the patient's bone;

said plate including an elongated central member extending from said base, the distal end of said central member having a first orthodontic appliance integrally formed therewith for receiving wire for attachment to a second orthodontic appliance attached to a patient's tooth;

(b) securely anchoring and affixing said bone plate to the bone with at least one bone anchor fastener not utilizing subperiodontal ossocointegration so that the base plate is securely attached to the bone and the central member extends through the soft tissue of the jaw adjacent a non-occusal surface of the teeth;

(c) affixing said first orthodontic appliance to at least a second orthodontic appliance attached to at least one tooth in the patient's mouth using orthodontic wire;

(d) adjusting said wire periodically until teeth or bite mal-alignment is corrected as determined by the orthodontist; and (e) after completion of the orthodontic treatment, disconnecting said first orthodontic appliance from said second orthodontic appliance, and removing said base by removing said bone anchor fastener.

* * * * *